United States Patent
Schnell et al.

(10) Patent No.: US 6,171,484 B1
(45) Date of Patent: Jan. 9, 2001

(54) BUBBLE TRAP HAVING INLET/OUTLET TUBE AND DOCKING PORT

(75) Inventors: William J. Schnell, Libertyville, IL (US); David S. Utterberg, Seattle, WA (US)

(73) Assignee: DSU Medical Corporation, Las Vegas, NV (US)

( * ) Notice: Under 35 U.S.C. 154(b), the term of this patent shall be extended for 0 days.

(21) Appl. No.: 09/159,298

(22) Filed: Sep. 23, 1998

Related U.S. Application Data

(63) Continuation-in-part of application No. 08/810,361, filed on Mar. 3, 1997, now Pat. No. 5,983,947.

(51) Int. Cl.$^7$ .................................................. B01D 19/00
(52) U.S. Cl. .............................. 210/188; 96/206; 96/220; 210/519; 604/122; 138/89
(58) Field of Search .................. 95/260, 262; 96/204, 96/206, 215, 220; 210/188, 436, 513, 519, 521, 801; 422/44–48; 604/4, 30, 80, 122, 123, 186, 190, 283, 905; 138/89, 96 R, 106, 109, 967

(56) References Cited

U.S. PATENT DOCUMENTS

| | | |
|---|---|---|
| 3,095,062 | 6/1963 | Neely . |
| 3,287,885 | 11/1966 | Sommer . |
| 3,342,019 | 9/1967 | Smythe . |
| 3,412,760 | 11/1968 | Franck . |
| 3,527,572 | 9/1970 | Urkiewicz . |
| 3,795,088 | 3/1974 | Esmond . |
| 3,908,653 | 9/1975 | Kettering . |
| 3,976,311 | 8/1976 | Spendlove . |
| 3,996,027 | 12/1976 | Schnell et al. . |
| 4,031,891 | 6/1977 | Jess . |
| 4,048,995 | 9/1977 | Mittleman . |
| 4,137,160 | 1/1979 | Ebling et al. . |
| 4,149,860 | 4/1979 | Kulik . |
| 4,293,413 | 10/1981 | Schnell . |
| 4,311,137 | 1/1982 | Gerard et al. . |
| 4,345,999 | 8/1982 | Sigdell et al. . |
| 4,368,118 | 1/1983 | Siposs . |
| 4,493,705 | 1/1985 | Gordon et al. . |
| 4,531,937 | 7/1985 | Yates . |
| 4,568,333 | 2/1986 | Sawyer et al. . |

(List continued on next page.)

FOREIGN PATENT DOCUMENTS

| | | |
|---|---|---|
| 0 058 325 | 8/1982 | (EP) . |
| 0 318 993 | 6/1989 | (EP) . |
| 0 350 675 | 1/1990 | (EP) . |
| 0 587 251 A1 | 3/1994 | (EP) . |
| 1 408 319 | 10/1975 | (GB) . |
| 1 554 810 | 4/1979 | (GB) . |

Primary Examiner—Joseph W. Drodge
(74) Attorney, Agent, or Firm—Garrettson Ellis Seyfarth Shaw

(57) ABSTRACT

A flow through bubble trap for fluid flow lines comprises a chamber-defining wall and a flow inlet/outlet tube at least substantially extending through the chamber and open at opposed tube ends to respectively define an inlet and an outlet of the bubble trap. The tube defines a flow inlet port and a flow outlet port within the chamber interior. A flow blocking partition closes the bore of the tube between the flow inlet and outlet ports. Additionally, the chamber defining wall carries a retaining-sealing member for removable, sealing connection with a tube connector of a fluid flow line. The retaining-sealing member is free of fluid flow connection with the interior of the chamber defined by the wall, and thus serves as a seal for connectors on tube ends of a set carrying the bubble trap. Also, the chamber defining wall has a bottom wall that defines a third port. A tubular member extends upwardly from the third port for most but not all of the height of the bubble trap to define a space between the open, upper end the tubular member and the top wall of the bubble trap.

20 Claims, 1 Drawing Sheet

U.S. PATENT DOCUMENTS

| | | |
|---|---|---|
| 4,617,012 | 10/1986 | Vaillancourt . |
| 4,622,032 | 11/1986 | Katsura et al. . |
| 4,643,713 | 2/1987 | Viitala . |
| 4,666,598 | 5/1987 | Heath et al. . |
| 4,681,606 | 7/1987 | Swan, Jr. et al. . |
| 4,722,725 | 2/1988 | Sawyer et al. . |
| 4,722,731 | 2/1988 | Vailancourt . |
| 4,734,269 | 3/1988 | Clarke et al. . |
| 4,867,739 | 9/1989 | Kawano . |
| 5,061,236 | 10/1991 | Sutherland et al. . |
| 5,061,365 | 10/1991 | Utterberg . |
| 5,071,413 * | 12/1991 | Utterberg ............................. 604/905 |
| 5,204,000 | 4/1993 | Stedman et al. . |
| 5,228,889 | 7/1993 | Cortial et al. . |
| 5,250,040 | 10/1993 | Parks et al. . |
| 5,328,461 | 7/1994 | Utterberg . |
| 5,356,376 | 10/1994 | Milijasevic et al. . |
| 5,358,481 | 10/1994 | Todd et al. . |
| 5,385,372 | 1/1995 | Utterberg . |
| 5,411,705 | 5/1995 | Thor et al. . |
| 5,429,595 | 7/1995 | Wright, Jr. et al. . |
| 5,441,636 | 8/1995 | Chevallet et al. . |
| 5,520,640 | 5/1996 | Utterberg . |
| 5,591,251 | 1/1997 | Brugger . |
| 5,683,355 | 11/1997 | Fini et al. . |
| 5,830,185 | 11/1998 | Block, Jr. ............................. 604/123 |
| 5,980,741 * | 11/1999 | Schnell et al. ........................ 210/188 |
| 5,983,947 * | 11/1999 | Utterberg ............................. 138/89 |
| 6,010,623 * | 1/2000 | Schnell et al. ........................ 210/188 |
| 6,019,824 * | 2/2000 | Schnell ................................ 210/188 |
| 6,051,134 * | 4/2000 | Schnell et al. ......................... 96/204 |

\* cited by examiner

U.S. Patent    Jan. 9, 2001    US 6,171,484 B1
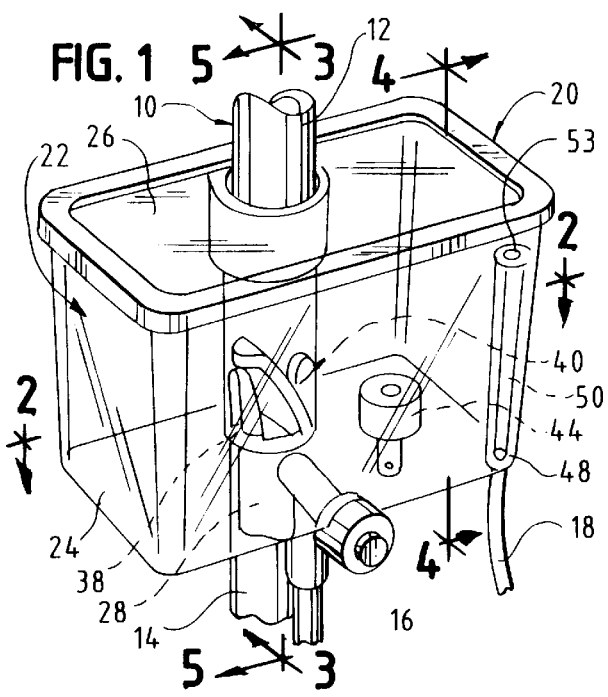
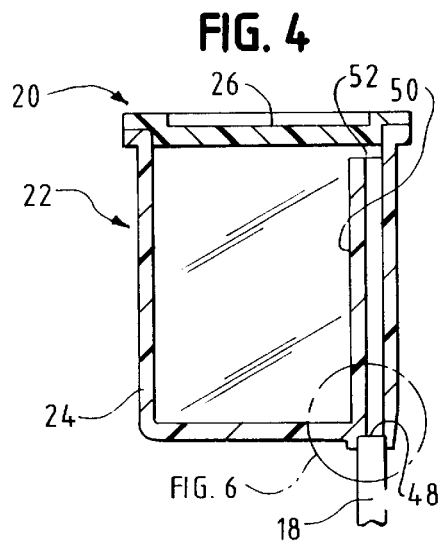
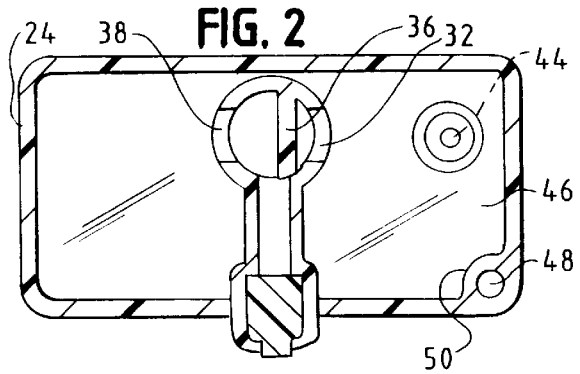
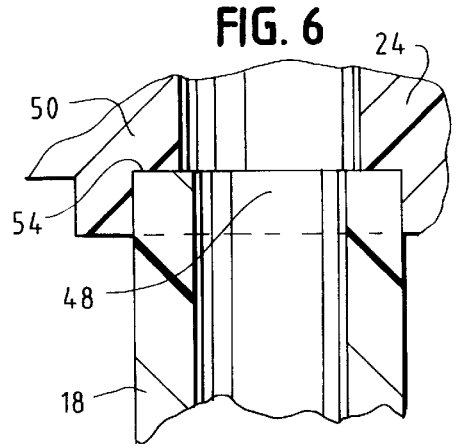
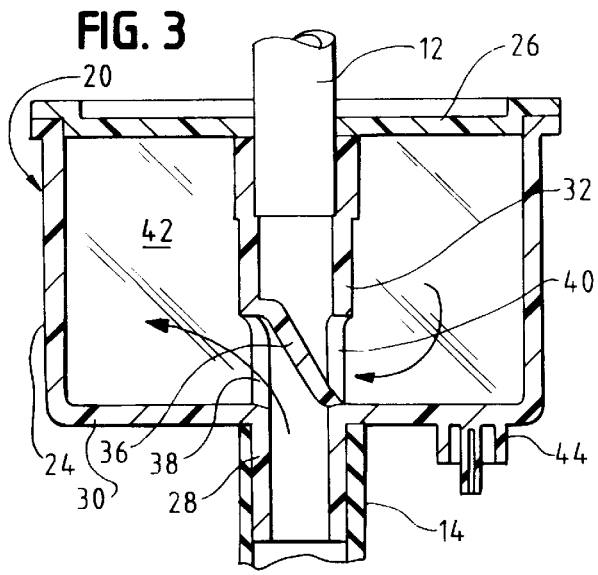
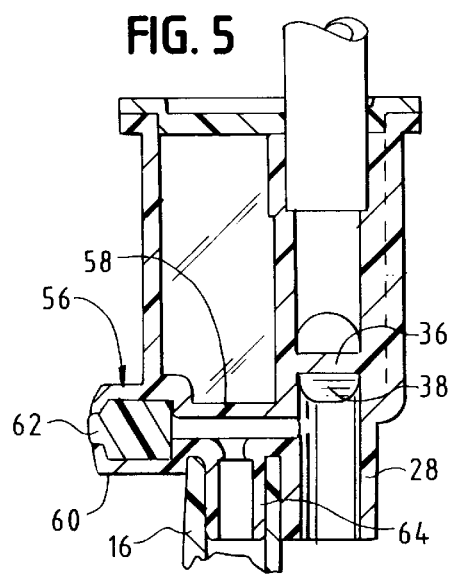

BUBBLE TRAP HAVING INLET/OUTLET TUBE AND DOCKING PORT

CROSS REFERENCE TO RELATED APPLICATION

This is a continuation-part of Utterberg Application Ser. No. 08/810,361, filed Mar. 3, 1997, now U.S. Pat. No. 5,983,947, issued Nov. 16, 1999.

BACKGROUND OF THE INVENTION

Bubble traps used in blood lines for hemodialysis or the like conventionally comprise a typically rigid or semi-rigid tube in which a blood inlet is provided to convey blood into the top of the chamber, while a blood outlet draws blood from the bottom of the chamber. Bubbles then are given the opportunity to rise to the top of the chamber so that the blood in the bottom of the chamber, which is withdrawn to pass through another portion of the blood set, is relatively free of bubbles, since they migrate to the top of the chamber.

See also Utterberg U.S. Pat. Nos. 5,328,461 and 5,520,640 as other examples of bubble traps for blood lines known to the prior art.

Typically, such bubble traps are higher than they are wide, to provide a deep, vertical chamber for the blood so that bubbles are kept away from the bottom of the chamber, from which the blood is being withdrawn. Typically, the prior art bubble traps have chambers with a vertical height that is more than twice their width. The height of the chambers of the prior art, coupled with the buoyancy of the incoming bubbles, is intended to counteract the downward bulk fluid flow of blood in the chamber toward the bottom outlet.

The inlets of the prior art blood chambers are variably positioned, the idea being that the blood entering through such inlets, and the bubbles contained in the blood, will initially stay in an upper portion of the chamber so that the bubbles have time to migrate upwardly through a liquid level to a gas space at the top of the chamber. Some inlets are vertically oriented, extending downwardly from the top of the chamber. Because of the height of the chamber, in flowing blood stops moving downwardly before the bubbles contained in it can be caught in the outlet flow. Other inlets of the prior art are vertically oriented in the bottom of the chamber, to propel the inlet blood upwardly toward the chamber top. Other inlets are horizontally oriented in the side of the chamber, so that the inlet flow must horizontally cross the downward flow of the bulk blood in the chamber, moving to an opposite sidewall where it is turned upwardly. This raises the possibility of bubbles being entrained in the downward flow before they are turned upwardly to reach the intended air space.

The bubble trapping principles of the prior art are effective with large, buoyant bubbles, typically having a volume greater than 50 microliters, and at relatively low blood flow rates of less than 300 ml. per minute. Blood chambers for trapping bubbles typically have volumes of about 15–25 ml. The buoyancy of the bubbles urges them to the surface at a velocity greater than the downward velocity of the bulk flow of the fluid in the bubble trap.

However, such bubble traps are increasingly ineffective as bubbles get smaller, and/or as flow rates increase. Modern dialysis techniques often require blood flow rates exceeding 450 ml. per minute, which raises the risk that bubbles can get through bubble traps of the prior art.

To accommodate such higher flows, the volumes of some designs of prior art bubble traps have been increased. However, this is distinctly undesirable, since that increases the priming volume of the set. It is highly desirable to keep the priming volume of any blood set low, since it is important to minimize the amount of blood removed from a patient at any one time during a blood treatment procedure such as dialysis.

Furthermore, another problem of prior art bubble traps, particularly those with the upwardly oriented inlets, is that they may require a flow diverter, to prevent blood at high flow rate from bursting through the blood-gas interface in a geyser-like action, which causes foaming of the blood and consequent clotting in the chamber. A typical blood flow diverter comprises an indentation in the wall of the bubble trap, to force the upwardly moving stream of inlet blood into a more horizontal flow, to prevent such geyser-like action. However, the diverter itself is not deemed desirable, and may result in an increased number of bubbles to be driven down toward the bottom outlet and thus to pass out of the bubble trap, contrary to that which was intended.

In accordance with this invention, solutions to the above technical problems are provided, resulting in an improved flow-through bubble trap for blood lines or the like, which is capable of processing blood at high flow rates of 450 ml. per minute and greater, while still retaining a low chamber interior volume.

In PCT International Publication WO98/23353, published on Jun. 4, 1998, wide bubble traps are disclosed in which the width of the bubble trapping chamber is preferably wider that the height of the chamber. The fluid inlet and fluid outlet to these chambers are then laterally spaced from each other to provide a fluid flow pattern which typically is substantially horizontal in nature, with less of a vertical flow component than in the prior art. This has been found to facilitate the migration of bubbles upwardly to the top of the chamber.

Also, the above International Publication shows a bubble trap in which blood inlet and blood outlet ports are positioned centrally and substantially coaxially, with blood being diverted horizontally into the chamber in one direction and then circulating around the chamber and being picked up laterally by flow in the same direction, and moved axially outwardly of the bubble trap. See particularly FIGS. 10–15 of the International Publication. This permits a significant size reduction in the bubble trap chamber, which, in turn, can result in a reduced blood volume in the chamber.

The improved, flow-through bubble trap of this invention for blood lines is capable of processing blood in high flow rates of 450 ml per minute or greater, while still retaining such a low chamber interior volume.

Also, medical fluid sets comprise lengths of tubing which are connected together with at least one tube connector component to connect the various tubing sections of the set together to form the set. Bubble trap chambers are included in said sets, including the types of bubble trap chamber in the previously described International Publication.

Such sets can be rather complex, having an array of branch tubings extending off from the main tubing pathway, one or more of such bubble trap chambers, and often a connected segment of a larger diameter pump tubing for installation in a peristaltic pump system.

The tubing ends of the sets carry connectors, typically luer lock connectors which have a removable closure to preserve sterility inside the set. Also, each of the set branch tubings are typically terminated with a connector and a removable cap to protect set sterility prior to use, to seal the tubing from leaking and/or to cover the opening of a typical connector after use. Also, some prior art teaches caps that are vented to provide a tortuous path for tubing sets that are to be gas sterilized. Other prior art such as Utterberg U.S. Pat. No. 5,385,372 shows a closure cap tube and end connector which is on a tether or a hinged arm that connects the cap with the connector. Also, caps may be threaded to better mate with luer lock connectors and/or having a male luer member to friction fit with a female luer socket.

Because many sets, particularly hemodialysis tube sets, have several branching tubes, there is a significant cost in providing all of the connectors with caps. Additionally, separate caps can be lost or may fall on the floor, which can cause a safety hazard. Caps are also subject to touch contamination in other ways, particularly as one hand must often be devoted to each of a cap and a set connector, as the two are brought together for the closing of the typical cap on the end of the connector.

By this invention, an improvement in bubble traps similar to those described in the above International Publication is provided, in which the number of separate caps which must be provided to a medical fluid set is reduced, or eliminated if desired, while the respective tubing connectors are still provided with apparatus for closing and sealing prior to use of the set and afterwards. Opening of the connectors may be provided by separation from a retaining, sealing member carried by the bubble traps of this invention.

DESCRIPTION OF THE INVENTION

By this invention, a flow-through bubble trap for fluid flow lines is provided, the fluid being typically extracorporeal blood. The bubble trap comprises a chamber defining wall, a flow inlet tube, and an outlet tube, the respective tubes being open as opposed tube ends to respectively define an inlet and an outlet of the bubble trap.

The respective tubes may be in coaxial relationship to each other and in abutting relation. They may be a single, integral piece if desired. The respective tubes or integral tube define a flow inlet port within the chamber interior and a flow outlet port within the chamber interior. Each of the flow inlet and flow outlet ports face laterally of the tube or tubes, with a flow-blocking partition closing the bore of the tube or tubes between the flow inlet and outlet ports.

Preferably, the chamber defining wall carries, as an integral part in rigid connection therewith, a retaining-sealing member for removable, sealing connection with a tube connector of a fluid flow line. The retaining-sealing member is free of fluid flow connection with the interior of the chamber defined by the wall. Preferably, the retaining-sealing member can be in the shape of a male luer or luer lock connector to receive a female luer in sealing rather than flow-creating relation, since the retaining-sealing member is free of fluid flow connection with the chamber interior. Alternatively, in the retaining-sealing member may be in the shape of a female luer or luer lock connector, or any other desired connector shape.

The chamber defined by the wall may be substantially rectangular in horizontal cross section, preferably with one horizontal dimension of the chamber being longer than the other horizontal dimension.

It is also preferable for the flow inlet and outlet ports to face away from each other so that flowing blood or other fluid initially passes into the chamber interior in a direction away from the flow outlet port. Then, the fluid circulates around within the chamber in substantially horizontal manner, permitting good opportunity for small bubbles to migrate upwardly, before the fluid reaches the flow outlet port to pass through the port and then axially outwardly through the chamber and beyond. Preferably, the flow inlet and flow outlet ports are both positioned adjacent to the bottom of the chamber, with the flow-blocking partition being positioned in a diagonal arrangement between the flow inlet and flow outlet ports, to prevent direct flow between them.

Additionally, the chamber preferably has a bottom wall that defines a third port. A tubular member extends upwardly from the third port for most but not all of the height of the bubble trap chamber, to define a space between an open, upper end of the tubular member and the top wall of the bubble trap. Thus, the chamber interior of the bubble trap communicates with the third port only through the tubular member at the open, upper end thereof. This can serve as a liquid level control within the chamber in that air and/or fluid can be inserted and/or removed through the third port and the tubular member. Also, parenteral solution, medication, and the like can be applied to the extracorporeal system through the third port and the tubular member.

Additionally, the flow inlet port can connect laterally in branching connection with a central manifold. A plurality of auxiliary ports communicate with the central manifold. One of the auxiliary ports comprises an injection port, typically with a needle-puncturable, resealable elastic member. The injection port is positioned longitudinally on the manifold so that an injection cannula can penetrate through the injection port and extend into main fluid flow adjacent the flow inlet port.

Another of the auxiliary ports communicating with the manifold may communicate in lateral, branching relation with the manifold and may also communicate with a length of flexible of tubing for connection with the source of intravenous solution, medication, or the like.

Thus, a tubular set for the transport of blood can be provided, which set comprises branching tubular conduits in a known, conventional arrangement, but containing the bubble trap of this invention, with the inlet and outlet of the bubble trap being typically connected to lengths of flexible tubing. Also, one of the inlet or outlet may be connected to roller pump tubing, if desired. Thus, the superior bubble removal of the chamber of this invention can be provided, along with one or more retaining-sealing members for removable sealing connection with a tube connector of one of the set fluid flow lines, so that removable caps may not be required for those end connectors of the fluid flow lines.

DESCRIPTION OF THE DRAWINGS

FIG. 1 is a fragmentary, perspective view of a portion of a blood handling set, showing an attached flow-through bubble trap in accordance with this invention;

FIG. 2 is a sectional view taken along line 2—2 of FIG. 1;

FIG. 3 is a sectional view taken along line 3—3 of FIG. 1;

FIG. 4 is a sectional view taken along line 4—4 of FIG. 1;

FIG. 5 is a sectional view taken along line 5—5 of FIG. 1; and

FIG. 6 is an enlarged, fragmentary view of a portion of FIG. 4.

DESCRIPTION OF SPECIFIC EMBODIMENTS

Referring to the drawings, a fragment of a tubular set 10 for the transport of blood is shown comprising lengths of flexible tubing 12, 14, 16, 18, which carry the conventional components of known blood transport sets, specifically for hemodialysis. The respective length of tubing 12–18 are shown to be connected to bubble trap 20 of this invention. Any known or desired design of tubular blood transport set may be used, with the novel bubble trap 20 serving as a substitute for known bubble traps in those prior sets.

Bubble trap 20 comprises a chamber-defining wall or housing wall 22, which specifically in this embodiment comprises an open top container 24 and a lid 26, which may be sealed in conventional manner to the open rim of container 24 by RF sealing, glue, or the like.

Container 24 defines a bottom aperture and port tubing 28, open to the container interior. Lid 26 defines an integral flow inlet/outlet tube 32 as a single piece which rests against the bottom wall 30 of container 24 to provide a sealed flow path from tube and aperture 28 through the chamber to the upper end of flow inlet/outlet tube 32, which defines an open aperture for receiving set tubing 12. Bottom tube 28 connects with flexible set tubing 14.

There is also defined, as an integral part of flow inlet/outlet tube 32, a diagonally positioned barrier wall 36, positioned to separate flow inlet port 38 and flow outlet port 40, each of which are defined in the wall of flow inlet/outlet tube 32.

Thus, blood can flow into bubble trap 20 upwardly through set tubing 14, passing through flow inlet port 38 into the interior 42 of bubble trap 20. As shown by the arrows, blood swirls in a largely horizontal manner around the interior of the chamber, providing adequate time for bubbles to rise to the top of the chamber. Then, blood is drawn into flow outlet port 40, passing upwardly through flow inlet/outlet tube 32 into flexible tubing 12. Flexible tubing 12 may comprise peristaltic or roller pump tubing if desired, for installation in a roller pump.

Further in accordance with this invention, molded container 24 may carry a co-molded component as an integral part in rigid connection therewith, namely retaining sealing member 44, which may be of the conventional shape of the front end of a male luer lock connector, to provide a removable, sealing connection with a tube connector of a fluid flow line, particularly a female luer lock connector of conventional design. Such a connector may be carried on the end of any of the flexible tube components of the blood set which carries bubble trap 20, so that it may be connected to retaining-sealing member 44, and thus does not require a sealing cap. While sealing caps must be separately molded and may exhibit the disadvantages discussed previously in this application, retaining-sealing member 44 may comprise an integrally molded part of container 24. It can be seen that a substantial advantage both of manufacture and in the use of the set can thus be provided. Multiple retaining sealing members 44 may be provided to bubble trap 20 for connection with the ends of multiple lengths of set tubings.

If desired, the flow of fluid through the bubble trap of this invention may take place in reverse direction from that described above, without significant loss of the bubble trapping capability and advantages of this invention.

The specific design and usage of retaining-sealing member 44 is similar in concept to that disclosed in Utterberg U.S. Ser. No. 08/810,361, filed Mar. 3, 1997, now U.S. Pat. No. 5,983,947.

It can be seen that container 24 and lid 26 are of rectangular, horizontal cross section, with inlet port 38 and outlet port 40 facing away from each other.

Further in accordance with this invention, the chamber defining wall 22 further defines a bottom wall 30 that defines a third port 48, which is surrounded by a tubular member 50 that extends upwardly from third port 48 for most but not all of the height of bubble trap 20. Space 52 is defined as particularly shown in FIG. 4 between an open, upper end 53 of tubular member 50 and the top wall 26 of the bubble trap. As previously described, this can serve as a liquid level controlling system for the bubble trap by the withdrawal or addition of air through tube 18 as may be desired. Also, it may be used for the addition of parenteral solution or medication to the blood flow path.

Tubular member 50 may be an integrally molded part of the wall of container 24. Also, a suitable recess 54 (FIG. 6) may be provided as a seat for flexible tube 18, which may communicate with a syringe for the addition or withdrawing of air from bubble trap 20, the withdrawing of blood samples, or the addition of blood or desired solution to the system.

Further by this invention, the inlet port tube 28, may connect laterally in branching connection with a central manifold 56, which comprises a tube 58 in branching connection with tube 28 at one end, and terminating in an injection port 60 at the other end. Injection port 60 is conventionally filled with a partition or plug of needle penetrable, resealable plastic material 62. Thus, it can be seen that an injection needle can extend through injection site 60 and its plug 62 of elastomeric material, and through tube 58 in axial manner, so that the needle tip can extend into an area of main fluid flow adjacent to or in flow inlet tube 28, as described in the above cited International Publication WO98/23353.

Also, a branching port tube 64 is provided in branch connection with manifold tube 58, for example to permit the administration of saline or other solution to the blood flow path within the set.

Thus, medication may be infused by a needle through injection site 60 directly into the bloodstream, with the needle passing the length of tubing 58 so that the needle tip is in the direct stream of flow in tube 28. Such a cannula may be a sharp cannula or a blunt cannula in the manner of the blunt cannula described in Utterberg U.S. Pat. No. 5,071, 413. The injection site 60 may carry a solid or slit elastomer partition 62, or it may comprise a branch line with a female luer connector, or a stop cock, or any other suitable flow control connection.

A toxic medication may be infused by a needle through injection site 60, while simultaneously infusing saline or other desired solution via tubing 16 and branch tube 64. The manifold tubing 58 allows a dilution space for mixing of the drug with saline, and then the blood.

An expensive or low volume drug may be infused by needle through injection site 60, followed by a saline flush through branch tube 64, which clears any residue drug from the manifold 56 and passes it into the main flow through tube 28. If desired, medication may be added through branch tubing 64.

By the above means, it can be seen that the number of access ports required on a blood conveying set can be reduced to two ports, which can serve every needed function of solution and medication administration.

Branch line 18 may also be used to connect to a pressure sensor, as well as being used for liquid level control.

Thus, an improved bubble trap is provided, having high flow bubble removing capability, and having releasable connection sites for connectors at tube ends of the set, so that separately manufactured closures for the connectors on tube ends may be eliminated. Also, an integral liquid level control device may be provided, as well as an all purpose solution and medication administration manifold.

The above has offered for illustrative purposes only, and is not intended to limit the scope of the invention of this application, which is as defined in the claims below.

That which is claimed:

1. A flow-through bubble trap for fluid flow lines, which comprises:

a chamber-defining wall;

a flow inlet/outlet tube at least substantially extending through said chamber and open at opposed tube ends to respectively define an inlet and an outlet of said bubble trap, said tube defining a flow inlet port within the chamber interior and a flow outlet port within the chamber interior, said flow inlet and flow outlet ports facing laterally of said tube; and a flow-blocking partition closing the bore of said tube between said flow inlet and outlet ports;

said chamber defining wall carrying, as an integral part in rigid connection therewith, a retaining-sealing member for removable, sealing connection with a tube connector of a fluid flow line, said retaining-sealing member being free of fluid flow connection with the interior of said chamber defined by said wall.

2. The bubble trap of claim 1 in which the chamber defined by said wall is substantially rectangular in horizontal cross section, one horizontal dimension of said chamber being longer than the other horizontal dimension.

3. The bubble trap of claim 1 in which said flow inlet and flow outlet ports face away from each other.

4. The bubble trap of claim 1 in which said retaining-sealing member is of the shape of a male luer.

5. The bubble trap of claim 1 in which said chamber defining wall has a bottom wall that defines a third port, and a tubular member extending upwardly from said third port for most but not all of the height of said bubble trap to define a space between an open, upper end of said tubular member and the top wall of said bubble trap.

6. The bubble trap of claim 1 in which said flow inlet port defines a tube which connects laterally in branching connection with a central manifold, a plurality of auxiliary ports communicating with the central manifold, one of said auxiliary ports comprising an injection port positioned longitudinally on the manifold so that an injection cannula can penetrate through said injection port and extend into main fluid flow adjacent the flow inlet port, another of said auxiliary ports communicating with said manifold and also communicating with a length of flexible tubing for connection with a source of intravenous solution.

7. The bubble trap of claim 6 in which said manifold is positioned adjacent to the bottom wall of said chamber.

8. The bubble trap of claim 1 in which said inlet and outlet ports are facing in opposite directions and occupy substantially the same tubular segment of said flow inlet/outlet tube, said flow blocking partition extending at an acute angle to the longitudinal axis of said flow inlet/outlet tube to close the bore thereof between said flow inlet and flow outlet ports.

9. The bubble trap of claim 8 in which said flow inlet and flow outlet ports are positioned near the bottom wall of said chamber.

10. A tubular set for the transport of blood, which set comprises the bubble trap of claim 1, with said flow inlet port and flow outlet port each being connected to lengths of flexible tubing.

11. The bubble trap of claim 1 in which at least one horizontal dimension of said chamber-defining wall is greater than a vertical dimension of said wall.

12. A flow-through bubble trap for fluid flow lines, which comprises:

a chamber-defining wall, the chamber defined by said wall being substantially rectangular in horizontal cross section, one horizontal dimension of said chamber being longer than the other horizontal dimension, and at least one of said horizontal dimensions being greater than a vertical dimension of said wall;

a flow inlet/outlet tube at least substantially extending through said chamber and open to opposed tube ends to respectively define an inlet and an outlet of said bubble trap, said tube defining:

a flow inlet port within the chamber interior and a flow outlet port within the chamber interior, said flow inlet and flow outlet ports facing laterally of said tube and away from each other; and a flow-blocking partition closing the bore of said tube between the flow inlet and outlet ports;

said chamber defining wall carrying, as an integral part in rigid connection therewith, a retaining-sealing member for removable, sealing connection with a tube connector of a fluid flow line, said retaining-sealing member being free of fluid flow connection with the interior of said chamber defined by said wall, said flow inlet and flow outlet ports being positioned near the bottom wall of said chamber.

13. The bubble trap of claim 12 in which said chamber defining wall has a bottom wall that defines a third port, and a tubular member extending upwardly from said third port for most but not all of the height of said bubble trap to define a space between an open, upper end of said tubular member and the top wall of said bubble trap.

14. The bubble trap of claim 13 in which said flow inlet port connects laterally in branching connection with a central manifold, a plurality of auxiliary ports communicating with the central manifold, one of said auxiliary ports comprising an injection port positioned longitudinally on the manifold so that an injection cannula can penetrate through said injection port and extend into main fluid flow adjacent the flow inlet port, another of said auxiliary ports communicating with said manifold and also communicating with a length of flexible tubing for connection with a source of intravenous solution.

15. A tubular set for the transport of blood, which set comprises the bubble trap of claim 12, with said flow inlet port and flow outlet port each being connected to lengths of flexible tubing.

16. A flow-through bubble trap for fluid flow lines, which comprises:

a chamber defining wall;

a flow inlet/outlet tube at least substantially extending through said chamber and open at opposed tube ends to respectively define an inlet and an outlet of said bubble trap, said tube defining:

a flow inlet port within the chamber interior and a flow outlet port within the chamber interior, said flow inlet and outlet ports facing laterally of said tube; and a flow-blocking partition closing the bore of said tube between said flow inlet and outlet ports;

said chamber defining wall having a bottom wall that defines a third port, and a tubular member extending upwardly from said third port for most but not all of the height of said bubble trap to define a space between an open upper end of said tubular member and the top wall of said bubble trap.

17. The bubble trap of claim 16 in which the chamber defined by said wall is substantially rectangular and horizontal cross section, one horizontal dimension of said chamber being longer than the other horizontal dimension, at least one of said horizontal dimensions of said chamber-defining wall being greater than the vertical dimension of said wall, said flow inlet and flow outlet ports facing away from each other.

18. The bubble trap of claim 17 in which said flow inlet port connects laterally in branching connection with a central manifold, a plurality of auxiliary ports communicating with the central manifold, one of said auxiliary ports comprising an injection port positioned longitudinally on the manifold so that an injection cannula can penetrate through said injection port and extend into main fluid flow adjacent the flow inlet port, another of said auxiliary ports communicating with said manifold and also communicating with a length of flexible tubing for connection with a source of intravenous solution.

19. The bubble trap of claim 18 in which said manifold is positioned adjacent to the bottom wall of said chamber.

20. A tubular set for the transport of blood, which set comprises the bubble trap of claim 16, with said flow inlet port and flow outlet port each being connected to lengths of flexible tubing.

* * * * *